United States Patent [19]

Cook et al.

[11] 4,037,465
[45] July 26, 1977

[54] ULTRASONIC PROBE SYSTEM FOR THE BORE-SIDE INSPECTION OF TUBES AND WELDS THEREIN

[75] Inventors: K. Von Cook; Dan W. Koerner, both of Clinton; Robert A. Cunningham, Jr., Powell; Horace T. Murrin, Jr., Alcoa, all of Tenn.

[73] Assignee: The United States of America as represented by the United States Energy Research and Development Administration, Washington, D.C.

[21] Appl. No.: 743,371

[22] Filed: Nov. 19, 1976

[51] Int. Cl.² .......................................... G01N 29/04
[52] U.S. Cl. .............................................. 73/67.8 S
[58] Field of Search .............. 73/67.8 S, 67.8 R, 67.7, 73/67.5 R, 67.9, 71.5 US

[56] References Cited

U.S. PATENT DOCUMENTS

| | | | |
|---|---|---|---|
| 3,028,752 | 4/1962 | Bacon | 73/67.8 R |
| 3,584,504 | 6/1971 | Proctor et al. | 73/71.5 US |
| 3,600,613 | 8/1971 | Clarke | 73/67.8 S |
| 3,646,805 | 3/1972 | Walters | 73/67.8 S |

Primary Examiner—Richard C. Queisser
Assistant Examiner—Stephen A. Kreitman
Attorney, Agent, or Firm—Dean E. Carlson; Stephen D. Hamel; Louis M. Deckelmann

[57] ABSTRACT

A probe system is provided for the bore-side inspection of tube-to-header welds and the like for small diameter tubes. The probe head of the system includes an ultrasonic transmitter-receiver transducer, a separate ultrasonic receiver, a reflector associated with the transducer to properly orient the ultrasonic signal with respect to a tube wall, a baffle to isolate the receiver from the transducer, and means for maintaining the probe head against the tube wall under investigation. Since the probe head must rotate to inspect along a helical path, special ultrasonic signal connections are employed. Through the use of the probe, flaws at either the inner or outer surfaces may be detected.

8 Claims, 9 Drawing Figures

ULTRASONIC PROBE SYSTEM FOR THE BORE-SIDE INSPECTION OF TUBES AND WELDS THEREIN

BACKGROUND OF THE INVENTION

This invention was made in the course of, or under, a contract with the Energy Research and Development Administration.

In the fabrication of tube-type heat exchangers, e.g., steam generators, a large number of tubes must be joined (usually welded) to one or more headers. This is frequently accomplished by providing pipe stubs extending from the headers and joining the end of exchanger tubes to the end of these stubs. When accessible, the joint may be inspected by one or more conventional means, e.g., dye-penetrant, radiography, etc. The degree of care exercised in this inspection depends upon the intended use of the heat exchangers; for nuclear systems, the testing is extensive and involves both radiographic and ultrasonic inspection techniques.

In the field of ultrasonic inspection, ultrasonic probes are available commercially which can be employed in the inspection of large diameter pipe. For such inspections, the two walls (inner and outer) are substantially flat in small regions under inspection by the probe. However, in small diameter tubes, such as those of 16 mm O.D., 2.79 mm wall thickness, the highly curved surfaces create a high degree of signal scatter and thus flaws are not easily determined, particularly those on or near the inner surface. Accordingly, there exists a need for an improved probe for the inspection of small diameter tubing. The present invention was conceived to meet this need in a manner to be described hereinbelow.

SUMMARY OF THE INVENTION

It is the object of the present invention to provide an ultrasonic probe system for the accurate inspection of small diameter tubing from the interior (bore-side) thereof.

The above object has been accomplished in the present invention by providing an ultrasonic probe system wherein the probe itself utilizes two transducers. The first transducer, having both transmitting and receiving capabilities, is directed parallel to the inside tube wall toward a reflector in the probe with the reflector set to produce a shear wave in the tube wall of about 45°. The second transducer directed perpendicularly to the inside tube wall in one embodiment is used only as a receiver. A baffle in the probe separates the transducers to prevent ultrasound scattered from the wall (from the first transducer) from reaching the second transducer. Biasing means maintains the baffle against the tube wall. A rotary contact unit on the probe drive permits the conveyance of signals to and from the probe so as to permit rotation and axial movement of the probe. The probe is adapted to be made with an O.D. of about 10 mm for example, such that the bore-side inspection of small diameter tubes can be effected. The use of the second receiver substantially increases the sensitivity of the read-out system. For example, without the second receiver, notches lessthan 0.25 mm on the inner surface of a tube being inspected cannot be deteced while the use of the second receiver effects detection of notches as small as 0.10 mm.

The second transducer-receiver in the probe has a different orientation in each of two other respective embodiments of the invention.

DESCRIPTION OF THE PREFERRED EMBODIMENT

Figure 1:
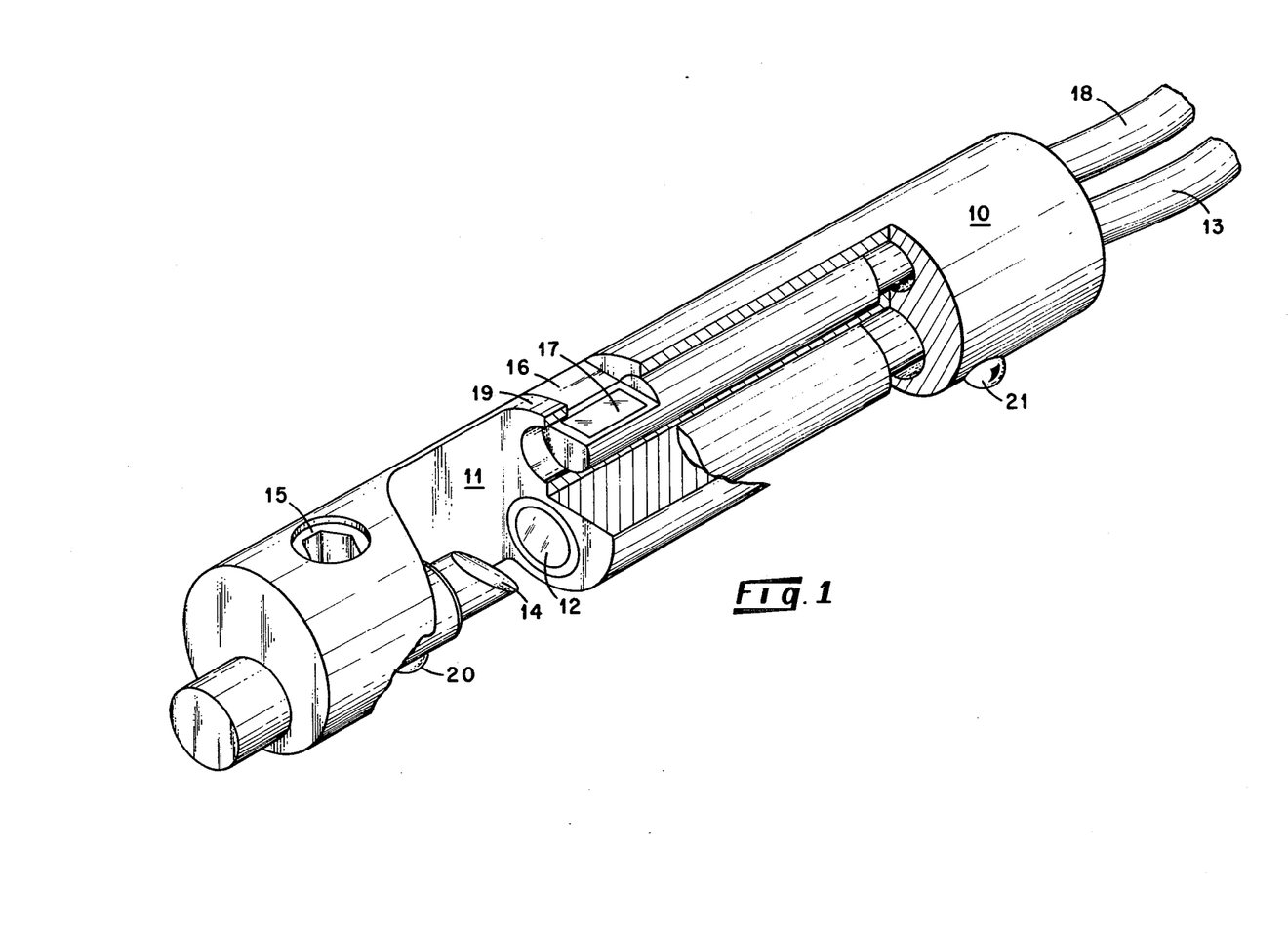
FIG. 1 is an isometric view, partly cutaway, of an ultrasonic probe of the present invention.

An improved ultrasonic probe for the bore-side inspection of small diameter tubes is shown in FIG. 1 of the drawings, wherein a cylindrical body member 10, having a diameter less than the bore of tubes to be inspected, is normally mounted on the end of a support, not shown. The forward end of the body 10 is provided with a deep recess 11. Facing axially and forwardly into this recess 11 is an ultrasonic transmitter-receiver transducer 12 suppllied from the electrical lead 13. Also facing axially, but rearwardly, into recess 11 is a reflector 14 aligned from the transducer 12. The relfector is adjustable in position and held in a desired position by a set screw 15. The angle of the reflector face (e.g., 55° from the tube axis) is chosen to provide the desired angle between the reflected ultrasonic signal and a tube wall (e.g., 20° from normal).

Rearward from the recess 11 is a small notch 16 oriented at 90° therefrom. Ultrasound receive 17 is mounted with body 10 so as to face radially outward in this notch. The receiver 17 is conntected to signal lead 18. The ridge 19 between recess 11 and notch 16 serves as a baffle between transducer-receiver 12 and receiver 17 to prevent the reception of ultrasound scattered from the interior surface of a tube under inspection. The body 10 is provided with biasing means, such as spring-loaded ball plungers 20, 21, to maintain the baffle 19 against the tube wall. Although not shown, locking means are provided for the transducer 12 and receiver 17 so that they may be individually removed if defective, or adjusted to a position to maximize signal strength.

As stipulated above, the probe body 10 is mounted at the end of a support arm, not shown, through which the electrical leads 13 and 18 are adapted to be encased. The support arm, in turn, is caused to move axially and rotationally by a pair of appropriate drive systems, not shown, mounted on a common support, not shown. Typically, the probe may be moved 0.0127 cm each revolution and rotated at 20 rpm. This causes the probe to inspect about 2.54 cm of pipe in ten minutes. Of course, inspection speed is variable and will depend upon the inspection mode, sensitivity, recording requirements, etc. For these weld inspections, a total of about 1.270 cm is required.

It is necessary to both supply an ultrasonic signal to one transducer 12 and receive a respective signal from the transducer 12 and the receiver transducer 17 throughout the duration of probe movement. This is complicated by the rotational motion. Conventional slip-ring types of the electrical devices create excessive noise in the signals; however, a rotary joint used in microwave applications has been found to be highly effective in minimizing signal degradation. Thus, the signal leads 13 and 18 are adapted to be coupled through such a rotary joint, not shown. One such typical joint is a Model 1279X Dual Channel Rotary Joint manufactured by the Kevlin Manufacturing Company, Wooster, Massachusetts.

Figure 2:
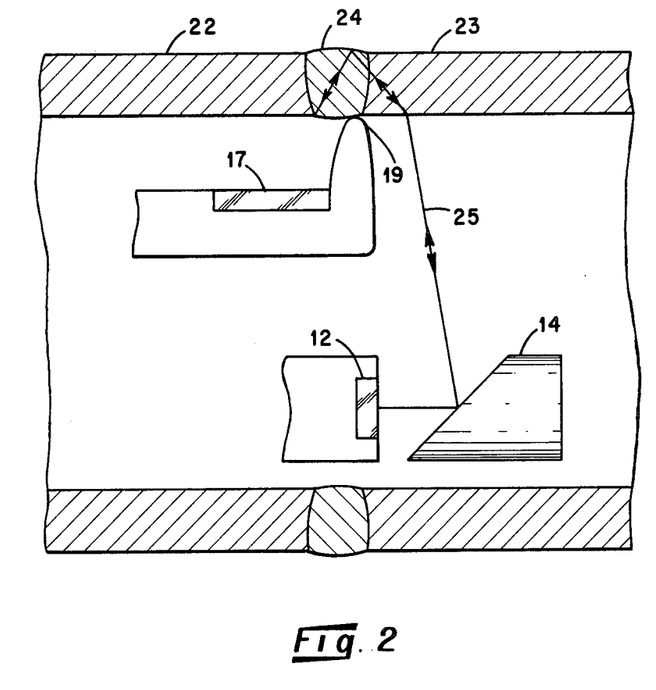
FIG. 2 is a drawing illustrating schematically, the operation of the probe of FIG. 1.

The operating principle of the present inspection system is illustrated in FIG. 2 of the drawings. An axially-oriented ultrasonic sound beam is emitted by the transmitter-receiver transducer 12. Due to the coupling medium, e.g., water, this ultrasonic beam is conveyed to the surface of the reflector 14 and thence to the interior of the tube 23 to be inspected, which tube is affixed to a tube sheet stub 22 by means of a weld 24. With the ultrasonic beam striking at an angle of about 20° from the normal, the sound wave is propagated in the tube 23 and the weld 24 as shown. This sound wave, when encountering a properly oriented impedance mismatch, such as a surface or a flaw, produces a second sound wave, a portion of which moves in an opposite direction along the path 25 until an electrical signal is received in the transducer 12.

In addition, another sound wave that is not as dependent on discontinuity orientation is propagated to the receiver transducer 17 which, in turn, produces an electrical signal. It may be seen that the baffle 19 isolates the receiver transducer 17 from sound waves scattered from the inner surface of the tube 23 so that only sound waves generated within the tube wall will give rise to detectable signals.

Figure 3:
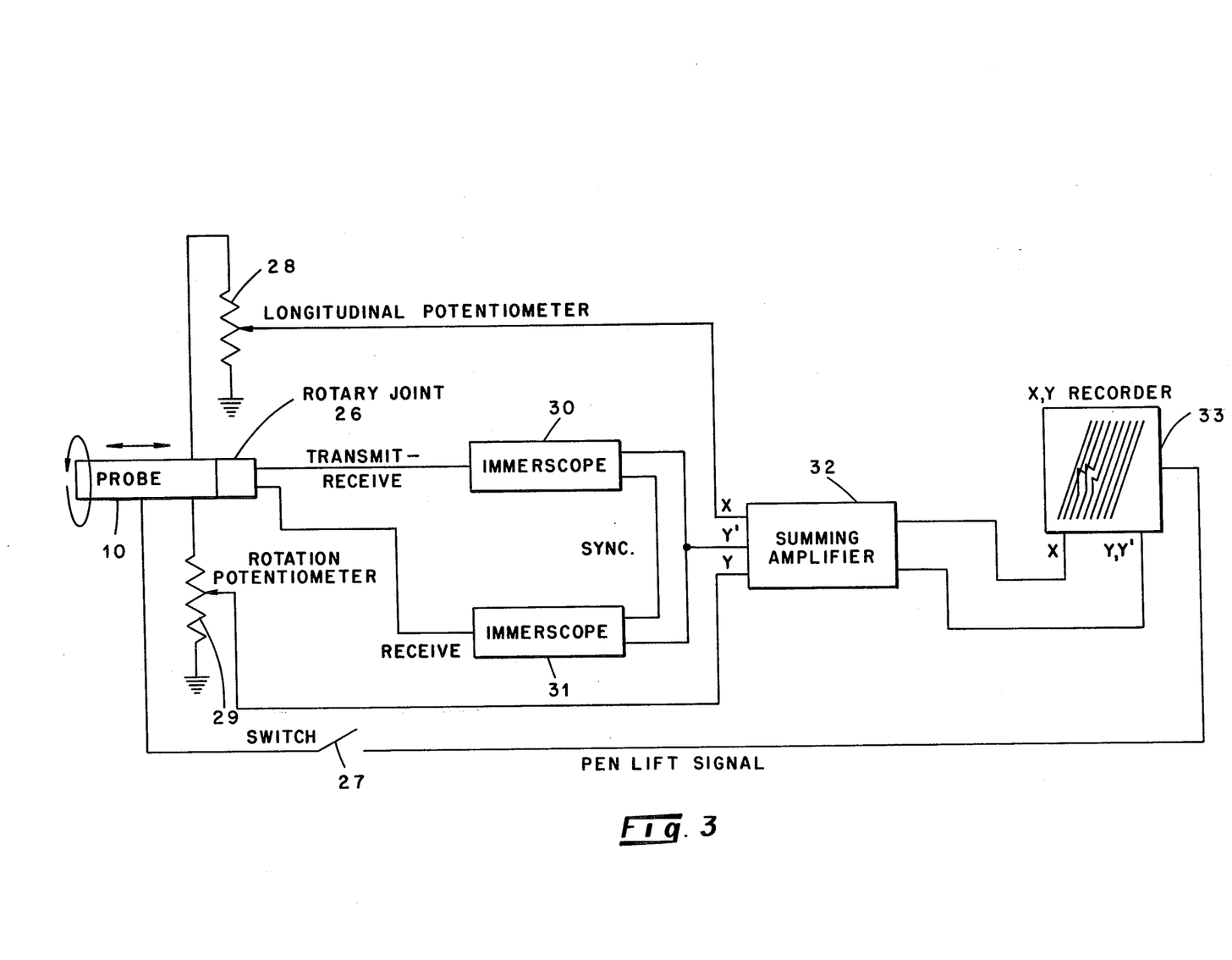
FIG. 3 is a block diagram of circuitry utilized with the probe of FIG. 1.

A typical circuit for dual channel ultrasound inspection is illustrated in block diagram form in FIG. 3. As shown, the rotary joint 26 on the end of the probe 10 is coupled on two conventional ultrasonic flaw detection units, such as Model 725 Immerscopes 30, 31. One of these (unit 30) is operated to transmit and to receive signals. The second (unit 31), which is triggered to synchronism with the first unit 30, acts only as a signal receiver. Flaw signal outputs in the form of voltages, Y', feed a summing amplifier 32 together with signals from a longitudinal position potentiometer 28 (X) and a rotational position potentiometer 29 (Y). Both X and Y + Y' voltages are input signals to an X-Y recorder 33, resulting in slanting trace lines during probe movement. Any value of Y' causes the trace to deviate in a Y-direction from the normal trace, as illustrated. Due to the finite speed of the recorder pen, only every other rotation is recorded as governed by a cam-operated swith 27. This permits the recorder pen to move from a top position to a bottom position prior to producing a succeeding trace.

Figure 4:
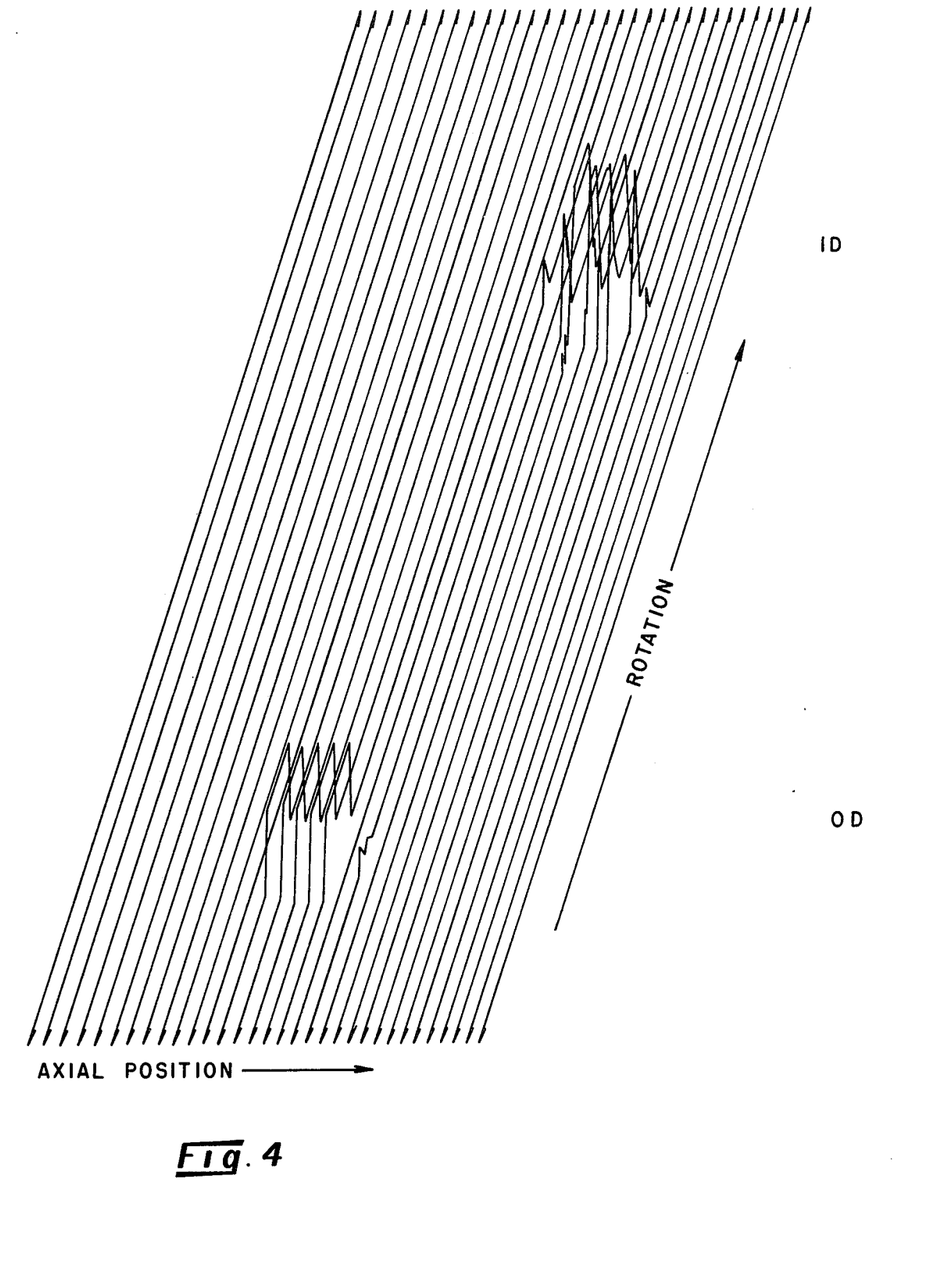
FIG. 4 is a typical scan recording obtained with the circuit of FIG. 3, illustrating the presence of simulated flaws near both the outer and inner walls of a tube weld.

FIG. 4 illustrates a typical recorder tracing obtained using a reference tube indicating a simulated flaw near the outer diameter of the tube as well as a simulated flaw near the inner diameter.

Figure 5:
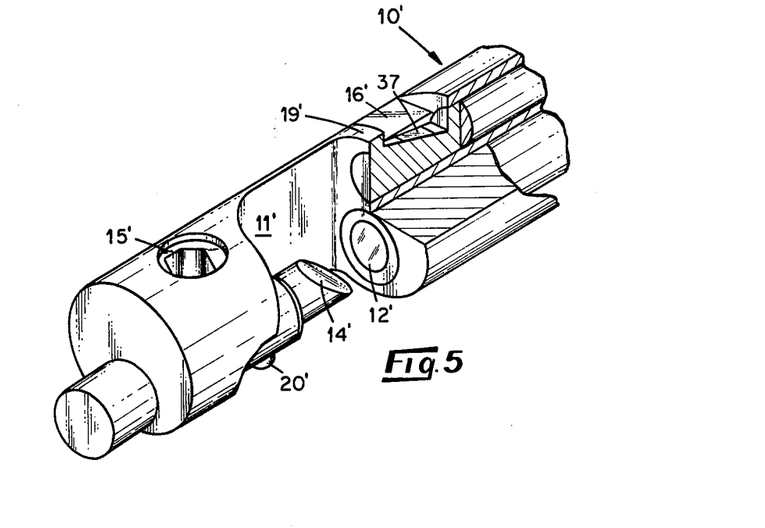
FIG. 5 is an isometric view, partly cutaway, of another probe of the present invention.

Another probe embodiment of the present invention is illustrated in FIG. 5 of the drawings, which is substantially the same as the device of FIG. 1, except the second transducer-receiver 17 of FIG. 1 has been replaced with a transducer-receiver 37 which, as can be seen in FIG. 5, is provided with an angled face with respect to the face of the notch 16.

Figure 6:
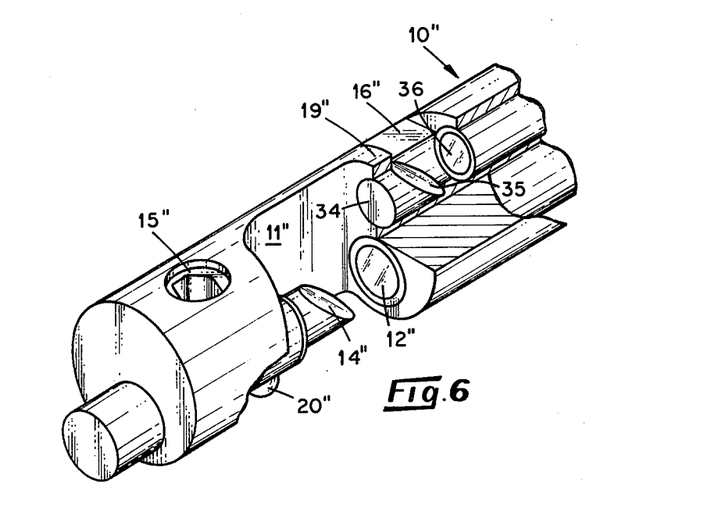
FIG. 6 is an isometric view, partly cutaway, of still another probe of the present invention.

Still another probe embodiment of the present invention is illustrated in FIG. 6 of the drawings, wherein the second transducer-receiver 17 of FIG. 1 is replaced with a receiver 36 as shown in FIG. 6. A member 34 is provided with an angled face 35 such that flaw signals received by the face 35 from the inside of a tube being inspected are reflected thereby onto the transducer-receiver 36. It should be noted and understood that the member 34 may be provided with suitable holes and/or slots, not shown, for attenuating any undesirable background signals to prevent or substantially reduce such signals reaching the receiver 36 during an inspection operation.

The probes of FIGS. 5 and 6 provide even more accurate read-out results than the probeof FIG. 1. It should be understood that all of the probes described above have a very small outside diameter and were illustrated in a much larger scale for the sake of clarity. A typical outside diameter for any of the disclosed probes is about 10 mm, for example.

Figure 7:
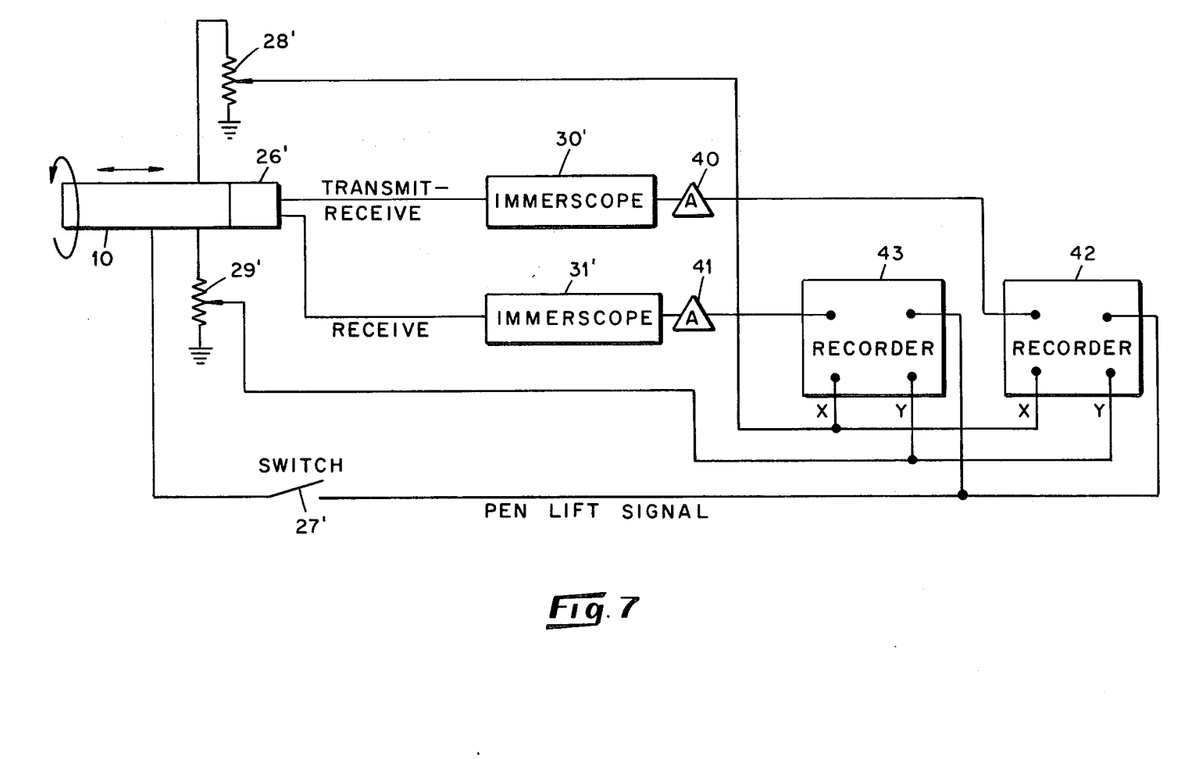
FIG. 7 is a block diagram of circuitry utilized with the probes of FIGS. 5 and 6.

It should be understood that either of the probes of FIGS. 5 and 6 may be connected to the read-out circuitry of FIG. 3, if desired. However, two separate recorders may be, and are preferably, utilized with either of the probes of FIGS. 5 and 6. Such a read-out circuit is illustrated in FIG. 7 of the drawings, wherein the analog voltage signal received by the Immerscope 30' is fed by means of an amplifier 40 to a recorder 42, and the analog voltage signal received by the Immerscope 31' is fed by means of an amplifer 41 to a recorder 43.

The longitudinal potentiometer 28' and the rotation potentiometer 29' provide the respective X and Y inputs to the recorders 42 and 43. It should be understood that respective conventional power supplies, not shown, are connected to the units 28' and 29'. A cam-operated switch 27' serves the same function as the switch 27 of FIG. 3, as described above.

The recorder 42 provides a record of any outside flaws of a tube being inspected by a given probe of the present invention as picked up by unit 30', while the recorder 43 provides a record of any inside flaws of the inspected tube, as picked up by the unit 30'.

Figure 8:
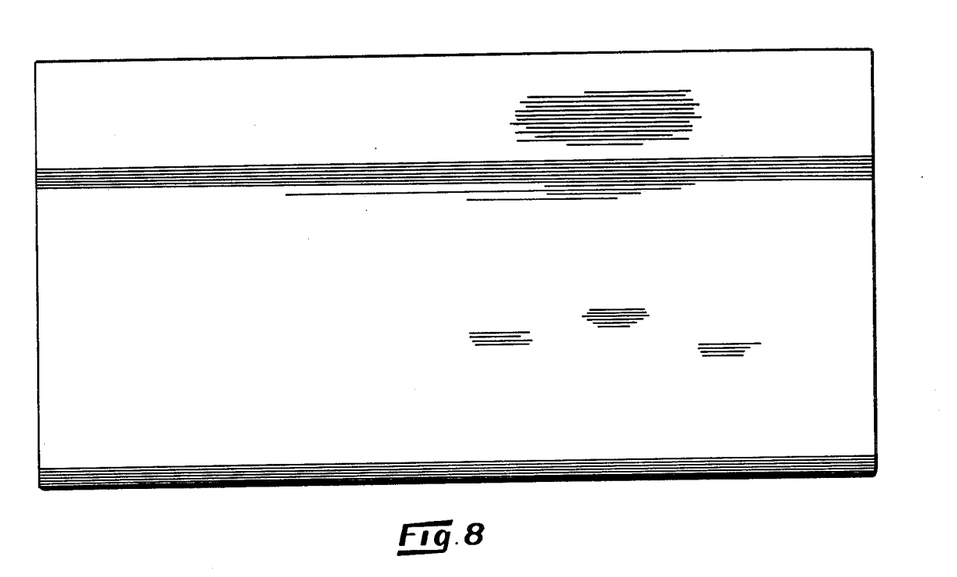
FIGS. 8 and 9 are typical scan recordings obtained with the circuit of FIG. 7, illustrating the presence of simulated flaws near both the outer and inner walls of a tube weld.
Figure 9:
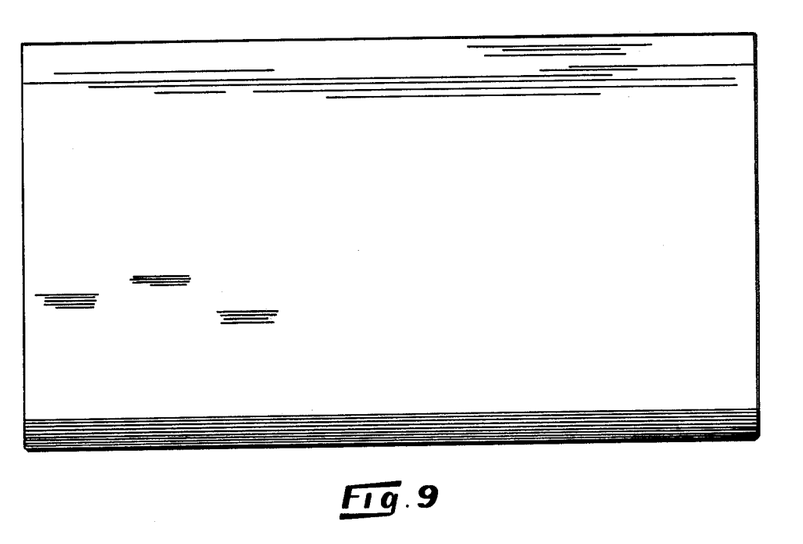

FIG. 8 is a typical recorder 42 tracing obtained using a reference tube indicating simulated flaws near the outer diameter thereof, and FIG. 9 is a typical recorder 43 tracing obtained using a reference tube indicating simulated flaws near the inner diameter thereof. It should be noted that the lines at the bottom of each trace are caused by one end of the tube being inspected.

The above-described probes and read-out systems were designed specifically for the inspection of tube-to-header joints in a heat-exchanger for nuclear applications. It should be understood that after the welding of each row of tubes, the respective weld joints and tubes will first be inspected by radiographic techniques. Any defect thus noted would be corrected. After the weld joints and tubes meet radiographic standards, they may then be inspected by means of one of the above-described probes and associated read-out system. This inspection would be repeated for each row of tubes.

It should be noted that prior art inspection probes are limited to a minimum I.D. of about 25.4 mm. Thus, the above-described invention meets the existing need for a probe that is capable of inspecting from the bore-side of a tube that has a minimum I.D. of about 10 mm.

This invention has been described by way of illustration rather than by limitation and it should be apparent that it is equally applicable in fields other than those described.

What is claimed is:

1. An ultrasonic probe system for the bore-side inpsection of small tubes and welds therein comprising a two-channel probe adapted to be rotated at a selected speed within a tube to be inspected and to be moved axially along said tube a selected amount for each revolution of said probe, said probe including a cylindrical body member, a first transmitter-receiver ultrasonic transducer mounted within said body member, a deep recess provided in the forward end of said body member, said first transducer facing axially and forwardly into said recess, a reflector mounted within said recess and aligned with said first transducer for receiving ultrasound therefrom and directing it into the wall of said tube at a desired angle, said reflector also receiving ultrasound reflected from said tube and directing it back to said first transducer, said body member further provided with a small notch oriented at 90° and rearward from with respect to said recess, a second ultrasnic receiver transducer mounted in said body memberwith the face thereof projecting into said notch for receiving ultrasonic signals from the inside wall of said tube, a ridge positioned between said recess and said notch which serves as a baffle between said respective transducers, said body member further provided with a separated pair of spring loaded biasing means for maintaining said ridge baffle against the inside wall of a tube being inspected, said system further including a first ultrasonic signal generator and receiver unit, an ultrasonic signal receiver unit, rotary joint means for coupling said respective units to said respective first and second transducers, recorder means, a longitudinal potentiometer actuated by axial movement of said probe, a rotation potentiometer actuated by rotary movement of said probe, said respective potentiometers providing respective X and Y inputs to said recorder means, and means for amplifying the received ultrasound outputs of said ultrasound units feeding them to said recorder means, whereby any flaws and/or defects on the outer and inner surfaces of said tube to be inspected are recorded by said recorder means.

2. The system set forth in claim 1, wherein said second receiver transducer is positioned to face radially outward in said notch.

3. The system set forth in claim 1, wherein said second receiver transducer is positioned at a desired inclined angle with respect to the base face of said notch.

4. The system set forth in claim 1, wherein said second receiver transducer faces axially and forwardly into said notch, and there is provided a second reflector mounted within said notch for directing ultrasound received from the inside wall of a tube being inspected onto said second transducer.

5. The system set forth in claim 1, wherein said ultrasonic units are connected to operate in synchronism, said amplifier means is a summing amplifier for receiving the combined outputs of said units, and said recorder means is a single recorder.

6. The system set forth in claim 3, wherein said recorder means comprises two separate recorders, one of said recorders providing a record of any sensed flaws on the outside wall of a tube being inspected by means of said first transducer and said first ultrasonic unit, and the other one of said recorders providing a record of any sensed flaws on the inside wall of the tube being inspected by means of a said second transducer and said second ultrasonic unit.

7. The system set forth in claim 4, wherein said recorder means comprises two separate recorders for recording the respective outside wall flaws and inside wall flaws of the tube being inspected.

8. The system set forth in claim 1, wherein said probe is adapted to be rotated at a speed of 20 rpm and moved axially 0.0127 cm for each revolution of said probe during a tube inspection operation.

* * * * *